United States Patent [19]  [11]  4,291,189
Bishkin  [45]  Sep. 22, 1981

[54] ALKYLATION PROCESS IMPROVEMENT

[75] Inventor: David B. Bishkin, Houston, Tex.

[73] Assignee: Monsanto Company, St. Louis, Mo.

[21] Appl. No.: 144,733

[22] Filed: Apr. 28, 1980

[51] Int. Cl.$^3$ ............................................... C07C 7/00
[52] U.S. Cl. ..................................... 585/860; 585/466
[58] Field of Search ................................ 585/860, 466

[56] References Cited

U.S. PATENT DOCUMENTS

| | | | |
|---|---|---|---|
| 3,240,833 | 3/1966 | Cash | 585/860 |
| 3,583,906 | 6/1971 | Basila et al. | 585/860 |
| 3,696,162 | 10/1972 | Kniel | 585/860 |
| 4,051,191 | 9/1977 | Ward | 585/466 |

Primary Examiner—Curtis R. Davis

[57] ABSTRACT

Entrained phosphoric acid contained in isopropylbenzene alkylate from a solid phosphoric acid-catalyzed process wherein benzene is alkylated with propylene is neutralized and rendered soluble in the alkylate by the addition to the alkylate stream of a primary amine.

7 Claims, No Drawings

ALKYLATION PROCESS IMPROVEMENT

FIELD OF THE INVENTION

This invention concerns the manufacture of monoisopropylbenzene by the alkylation of benzene with propylene in the presence of so-called solid phosphoric acid catalyst. The invention is particularly directed to removal and disposal of phosphoric acid which remains in the alkylate which has contacted a solid phosphoric acid.

DESCRIPTION OF THE PRIOR ART

Mono-isopropylbenzene (also known as "cumene") is important as a constituent of gasoline-boiling-range motor fuels of high antiknock value. It is also in considerable demand as an intermediate in the synthesis of higher molecular weight aromatic hydrocarbons such as cumene and other polyalkylated benzene hydrocarbons containing at least one isopropyl group per molecule. More recently, it has become especially important as an intermediate in the manufacture of phenol.

The use of solid phosphoric acid catalyst for various hydrocarbon alkylation and polymerization reactions has been known for some time. It has also been established that this catalyst is susceptible to deterioration and that in use the phosphoric acid deposited on the solid catalyst support is slowly entrained and carried off of the support by the liquid hydrocarbons leaving the alkylation reactor. Phosphoric acid in the alkylate is quite corrosive to carbon steel vessels and piping; accordingly, it has previously been necessary to employ stainless steels or other more expensive materials of construction downstream of the alkylation reactor.

SUMMARY OF THE INVENTION

It is an object of this invention to provide a method of neutralizing and removing entrained phosphoric acid from isopropylbenzene-containing alkylates.

A further object is to convert the phosphoric acid to a form which is non-volatile to prevent its contaminating the mono-isopropylbenzene in subsequent distillation operations in which the mono-isopropylbenzene is purified and separated from heavy components such as di- and poly-isopropylbenzenes.

Yet another object is to convert the entrained phosphoric acid to a form which is soluble in the alkylate to prevent its settling out in low spots in the system downstream of the alkylation reactor.

These and other objects are achieved by injection of a primary amine into the alkylate stream which contains entrained phosphoric acid. Quite surprisingly, it is critical to this invention that the amine employed be a primary amine; although it is well known that secondary and tertiary amines will form quaternary amine salts with acids such as phosphoric acid, the secondary and tertiary amines do not meet the criteria of reactivity, solubility and stability of the resulting amine phosphate at high temperatures necessary to achieve the objects of this invention.

DESCRIPTION OF PREFERRED EMBODIMENTS

Benzene for use as reactant in the process to which this invention relates is obtainable from several sources including the distillation of coal, the dehydrogenation of naphthenic hydrocarbon fractions containing cyclohexane, and the dehydrogenation and cyclization of aliphatic hydrocarbons containing 6 carbon atoms per molecule in straight-chain arrangement, such as normal hexane and the straight-chain hexenes.

Propylene utilized as alkylating agent in this process may be obtained from gases produced in the cracking of petroleum hydrocarbons, by the dehydration of propyl or isopropyl alcohols, and by any other suitable means which result in the formation of either substantially pure propylene or a hydrocarbon fraction containing substantial amounts of this olefinic hydrocarbon. Such fractions containing propylene also generally contain certain amounts of propane when they are derived from gases produced by cracking or dehydrogenation of hydrocarbons. It has been found that propylene-propane mixtures containing as little as 33% propylene, when used in accordance with the conditions prescribed by the present invention, give propylene conversions substantially equivalent to conversions obtained from fractions containing 95% propylene or more. Moreover, the yield of mono-isopropylbenzene, based upon the propylene converted, will be at least as high when using a $C_3$ fraction containing substantial amounts of propane as when using a fairly pure propylene fraction.

Solid phosphoric acid catalysts utilized in the present alkylation process are of the type well known to the art. They may be made by mixing an acid of phosphorous such as ortho-, pyro-, or tetra-phosphoric acid with a finely divided generally siliceous solid carrier (such as diatomaceous earth, prepared forms of silica, raw and acid-treated clays and the like) to form a wet paste; calcining at temperatures generally below about 500° C. to produce a solid cake; grinding and sizing to produce particles of usable mesh. The catalyst preparation procedure may be varied by forming particles of the original paste, by extrusion, or by pelleting methods, after which the formed particles are calcined.

In effecting reaction between benzene and propylene in the alkylation process, the reactant hydrocarbons are subjected to contact with the solid phosphoric acid catalyst at a temperature within the range from about 204° to 260° C. It has been found that at temperatures within this range the reaction proceeds at a practicable rate; at temperatures above this range the tendency toward side reactions and toward carbonylation of the catalyst becomes severe, and the increased rate of reaction brings about extremely different temperature conditions between the inlet and outlet of the catalyst bed.

The process is performed at pressures substantially within the range of from 25 to 60 atmospheres. Pressures in this range are necessary at the aforesaid temperatures to assure maintenance of at least a portion of the reactants in liquid state, which generally enhances the catalyst life. Subjection of the benzene and propylene reactants to contact with the catalyst in a proportion of at least 3 mols of benzene per mol of propylene is necessary in accordance with the process of the invention to achieve maximum yields of mono-propylated benzene, minimum formation of propylene polymers and also to assure maintenance to a substantial proportion of liquid phase material, as mentioned above. A proportion of benzene to propylene greater than 8:1 does not have any material effect on the desired reaction and imposes an unnecessary burden on the product fractionation.

The alkylate product from the alkylation process may be separated into its component hydrocarbon fractions by conventional and well-known distillation techniques.

Commonly, unreacted benzene and propylene are removed from the alkylate product by fractionation and recycled to the alkylation reactor inlet. Mono-isopropylbenzene is then removed as the desired product, again by fractionation and the heavy products, princiapply di- and poly-isopropylbenzenes may be disposed of as fuel or by other known means.

In accordance with the present invention, a primary amine is injected into the phosphoric acid containing alkylate stream downstream of the alkylation reactor. Although the primary amine may be injected at any point into the process, the objects of this invention are more fully realized if the injection is done as close as practical to the alkylation reactor outlet in order to neutralize the corrosive phosphoric acid as quickly as possible.

The alkylate stream leaving the alkylation reactor after contact with the solid phosphoric acid catalyst will typically contain dissolved phosphoric acid in amounts from about 5 to about 15 parts per million by weight. Additionally, the alkylate will typically contain undissolved entrained phosphoric acid in amounts from about 10 to about 50 parts per million by weight. During the purification process set out above, the phosphoric acid will be concentrated to levels typically in the range of 800 to 2000 parts per million in the heavy di- and polyisopropylbenzene stream.

Suitable amines for use according to the present invention are those having the formula $RNH_2$ wherein R is an organic radical and may be alkyl, aryl, aralkyl or alkenyl. Desirably, for reasons of economy, R is an alkyl radical having 6 to 20 carbon atoms. More preferably, R is an alkyl radical having 8 to 16 carbon atoms. To achieve fully the objects of the present invention as set out above, the radical R should be selected such that the primary amine and its phosphoric acid salt are soluble in di- and polyisopropylbenzenes and such that the amine is less volatile than isopropylbenzene so as not to be driven overhead in the distillation column in which this product is recovered.

The primary amine of the present invention is injected into the alkylene stream in amounts sufficient to give an amine/phosphoric acid molar ratio of from about 0.2:1 to about 1:1, although greater amounts of the primary amine may be employed. More preferably, the primary amine is used in a molar ratio to the phosphoric acid of about 0.3 to about 0.5.

The present invention is illustrated by the following examples, which are not intended as limiting the invention in any way.

EXAMPLE 1

To show that insoluble phosphoric acid is converted to a hydrocarbon-soluble, thermally stable, nonvolatile form by addition of a primary amine according to this invention, the following experiment was performed.

Approximately 300 ml of di-isopropylbenzene containing small amounts of poly-isopropylbenzenes was placed in a boiling flask fitted with a reflux condenser. To this material was added 700 parts per million (ppm) by weight of phosphoric acid ($H_3PO_4$). The material was then refluxed at a temperature of 210° C. for several hours. Analysis after four hours of refluxing showed about 165 ppm $H_3PO_4$ dissolved in the organic phase, and analysis after six hours refluxing showed about 140 ppm dissolved $H_3PO_4$.

To the refluxing flask was then added sufficient dodecylamine ($C_{12}H_{25}NH_2$), a primary amine, to give a molar ratio of amine: $H_3PO_4$ of 0.50. Continuing to reflux the mixture, samples of the organic phase were taken four, eight, and nine hours after addition of the amine, and the following data were obtained:

| Hours after Amine Addition | ppm Dissolved Phosphate |
|---|---|
| 4 | 640 |
| 8 | 697 |
| 9 | 670 |

EXAMPLES 2–4

To show the criticality of primary amines in the method of the present invention, the following experiments were performed.

Using the apparatus and procedure of Example 1, a tertiary amine (tributylamine) and two secondary amines (diamylamine, and a mixture of alkyl-substituted pyridines having an average molecular weight of 240 and boiling in the range of about 204° C. to about 361° C.) were added to the reflux flask. The following data were obtained:

| Example 2 Tributyl Amine | |
|---|---|
| Hours of Refluxing Before Amine Addition | ppm Phosphate in Organic Phase |
| 4 | 87 |
| 6 | 82 |
| 8 | 75 |
| Hours of Refluxing After Amine Addition | |
| 2 | 92 |
| 5 | 94 |
| 9 | 92 |

| Example 3 Diamyl Amine | |
|---|---|
| Hours of Refluxing Before Amine Addition | ppm Phosphate in Organic Phase |
| 4 | 32 |
| 8 | 38 |
| Hours of Refluxing After Amine Addition | |
| 4 | 180 |
| 8 | 167 |

| Example 4 Mixed Alkyl Pyridines | |
|---|---|
| Hours of Refluxing Before Amine Addition | ppm Phosphate in Organic Phase |
| 4 | 113 |
| 8 | 118 |
| 12 | 107 |
| Hours of Refluxing After Amine Addition | |
| 3.5 | 110 |
| 8 | 102 |

I claim:

1. A method of neutralizing and rendering entrained phosphoric acid soluble in isopropylbenzene alkylate comprising addition to said alkylate and said entrained phosphoric acid in amount of a primary amine effective to neutralize and render said phosphoric acid soluble.

2. A method according to claim 1 wherein said primary amine is added in a molar ratio of at least 0.2:1.

3. A method according to claim 1 wherein said primary amine is added in a molar ratio of from 0.3:1 to 0.5:1 to said acid.

4. A method according to claim 1 wherein the organic radical of said amine contains 8 to 16 carbon atoms.

5. A method according to claim 1 wherein the organic radical of said amine contains 8 to 16 carbon atoms.

6. A method according to claim 1 wherein said amine is less volatile than monoisopropylbenzene.

7. A method according to claim 6 wherein said amine is an alkylamine.

* * * * *